(12) United States Patent
Massoni (10) Patent No.: US 7,419,510 B2
(45) Date of Patent: Sep. 2, 2008

(54) HIGH AQUEOUS OXIDATION HAIRCOLOR SYSTEM

(75) Inventor: Jack Massoni, New Fairfield, CT (US)

(73) Assignee: Combe Incorporated, White Plains, NY (US)

( * ) Notice: Subject to any disclaimer, the term of this patent is extended or adjusted under 35 U.S.C. 154(b) by 0 days.

(21) Appl. No.: 11/199,107

(22) Filed: Aug. 8, 2005

(65) Prior Publication Data

US 2006/0037153 A1 Feb. 23, 2006

Related U.S. Application Data

(60) Provisional application No. 60/602,753, filed on Aug. 19, 2004.

(51) Int. Cl.
*A61Q 5/10* (2006.01)

(52) U.S. Cl. .............. 8/405; 8/406; 8/435; 8/552; 8/558; 8/611; 8/678

(58) Field of Classification Search ............... 8/405, 8/406, 435, 552, 558, 611, 678
See application file for complete search history.

(56) References Cited

U.S. PATENT DOCUMENTS

2001/0023515 A1 * 9/2001 Cottard et al. ............... 8/406

* cited by examiner

*Primary Examiner*—Eisa B Elhilo
(74) *Attorney, Agent, or Firm*—James V. Costigan; Hedman & Costigan, P.C.

(57) ABSTRACT

The invention provides an oxidation hair color system consists essentially of a dye phase and a developer phase, wherein the dye phase includes: a) a water soluble nonionic surfactant; b) a water soluble anionic polymer; c) water; d) oxidation dye intermediate; e) dye antioxidants and stabilizers and wherein the developer phase includes: a) secondary ethoxylated fatty alcohols; b) an oxidizer and c) water.

15 Claims, 2 Drawing Sheets

Secondary ethoxylated fatty alcohols used in the developer phase

Fig. 1

HIGH AQUEOUS OXIDATION HAIRCOLOR SYSTEM

This application claims the priority of Provisional Application Ser. No. 60/602,753, filed Aug. 19, 2004.

BACKGROUND OF THE INVENTION

Oxidation haircoloring products have dominated the world market over the past 50 years as the preferred method of changing the color of gray or pigmented hair for both men and women. These products are also referred to as "permanent haircolors", as they permanently alter the hair's coloration. Reapplication occurs as the hair's new growth becomes noticeable. Oxidation hair dyes are normally sold in the form of a two-component kit. In one container is an alkaline composition that contains oxidative dyes and an appropriate vehicle. In the other container is a developer composition that utilizes an oxidizing agent, usually hydrogen peroxide. The two compositions are mixed immediately prior to use and applied to the hair. The alkaline pH of the mixture causes the hair shaft to swell, allowing the dye precursors to penetrate into the cortex of the hair. These dye precursors are then oxidized, which combine to form larger molecules. These larger molecules contain a significant level of resonance, hence producing a colored product that is visible from the exterior of the hair. After an appropriate development time, the mixture is rinsed from the hair. The color of the hair is then permanently altered. Depending upon the pH of the mixture and strength of the developer, these systems can have the capability to lighten the hair's natural pigment, or only deposit color without the lightening action. The actual time that the mixed haircolorant is on the hair varies widely depending upon the product and desired affect, although it is generally 5 to 45 minutes before rinsing occurs. As the development time is a necessity, the viscosity of the mixture and its Theological properties are of significant importance to the product's overall performance.

The most common product form for oxidation haircolor products is to have both the dye and developer components as flowable liquids. That way the dye portion can be easily poured into an oversized developer bottle containing the oxidizer, and quickly mixed with moderate agitation. The consistency of the resulting mixture and the formulas that comprise these systems are of considerable importance to haircolor manufacturers. Traditional dye/developer systems relied upon tint phases with low levels of water and insoluble surfactants dissolved in organic solvents. Typically these formulas would have less than 30% water. The developers would be simple solutions of water and 3 to 12% hydrogen peroxide. As the two solutions are mixed, the high water content in the developer would precipitate out the water insoluble surfactants. With careful selection of surfactants for the tint phase, this precipitate would be in the form of a gel. The net result would yield a flowable gel mixture with thixotropic rheological features to allow for easy dispensing from a narrow applicator tip, while producing acceptable stay-put properties after application to the hair.

These types of systems were considered ideal for two component haircolorants, and have undergone little change since their inception. One improvement is taught in U.S. Pat. No. 6,187,058, where the volatile organic solvents are replaced with non-volatile materials, allowing for more environmentally friendly products to be marketed. A major departure from the low water haircolor systems evolved as a particular type of water insoluble anionic polymer was developed in the 1980's. First marketed as Acrysol ICS, and later under the Aculyn trademark by Rohm & Haas, Acrylates/Steareth-20 Methylacrylate Copolymer was found to be stable in hydrogen peroxide and form a thin, liquid dispersion in such systems. Today there are a host of similar materials that are commercially produced and can be described as; polymers of an ester of a fatty carboxylic acid and a polyalkylene glycol ether of a fatty alcohol and two or more monomers of fatty carboxylic acids or their esters.

For simplicity sake these can be referred to as water insoluble Acrylate Copolymers. Once these developers which are formulated with the specified copolymers come in contact with an alkaline solution, the entire mixture will thicken by polymer neutralization and solubilization. This allowed for the development of the so-called "high aqueous" dye phase of haircoloring products. These inventions simplified the formulation of this portion of the haircolor components. Typically they contain 50% or more water, a limited quantity of surfactants and organic solvents, along with dye intermediates and antioxidants. The first invention to describe this technology was in Re. 33,786, where the Acrysol ICS was the only compound mentioned. Since this time, modifications to polymers and composition attributes have been developed. These include the addition of various conditioning compounds as described in U.S. Pat. Nos. 5,376,146 and 5,393,305. U.S. Pat. No. 6,660,045 teaches the preparation of a creme using an acrylates copolymer in the developer, although with the large number of ingredients listed in the formulations this invention has lost its high aqueous nature. In general, these types of hair color systems have worked well, although the rheology produced by the acrylates copolymers alone is more Newtonian in nature, and tends to run off the hair. In practice, these systems have to be modified with the addition of other thickeners to produce a thixotropic product. This will rendered these formulas less efficient. Other Polymers of similar utility but are water soluble, most notably homo and copolymers of acylic acid crosslinked with a polyalkenyl polyether sold under the Carbopol brand by Noveon Corp. can be used in similar fashion, but lack the peroxide stability necessary for shelf life of finished products.

The object of this invention is to provide alternate formulations and manufacturing methods to achieve a high aqueous haircolor system suitable for use with any conceivable type of oxidation colorant. These formulations use known cosmetic ingredients in unique combinations which produce unexpected thickening properties upon mixing of both system components. There are additional advantages over traditional thickening systems and previously invented high aqueous products. These improvements over existing technology include: 1) Ease of formulation and manufacture, 2) Lower cost of ingredients, 3) More efficient dying system (less dyes required), 4) Improved gray coverage of finished products, 5) Superior theological benefits without the need for additional surfactants, 6) Safer for consumers and the environment, with no monomers present as with formulations that contain Aculyn.

SUMMARY OF INVENTION

The invention includes a specific oxidation haircolor dye phase that is used in combination with the system's developer. When combined, the resulting formula will yield a high aqueous vehicle to deliver standard oxidation dye components to the hair with an appropriate consistency to allow for ease of application through a typical haircolor applicator tip and create excellent stay-put properties. Both phases of the system must be flowable so as to allow for rapid transfer of the dye portion into a developer bottle, and facilitate ease of mixing.

The dye phase should contain the following ingredients:
1. 75-90 wt % water
2. 5-10 wt % of a water soluble nonionic surfactant selected from the group consisting of alkyl polyglycosides
3. 0.5-1.0 wt % of a carbomer.

The developer phase of the system should contain the following ingredients:
1. 60-84 wt % water
2. 15-25 wt % of secondary ethoxylated fatty alcohols or alkylphenol ethoxylates or a combination of both materials
3. 1-12 wt % of hydrogen peroxide or other suitable oxidizer

DETAILED DESCRIPTION OF THE INVENTION

Other ingredients typically used in oxidation haircolors such as primary intermediates, couplers, antioxidants, and chelating agents would be used in conjunction to the vehicle listed above. The developer portion of this system should contain the normal oxidizers used in a permanent haircolor, typically hydrogen peroxide at 1-12 wt % levels and any necessary stabilizers and chelating agents. These ingredients are added to 15-25 wt % of specific nonionic surfactants combined to achieve fairly narrow working HLB (hydrophilic/lipophilic balance) ranges. The materials that work best for this application fall into the general class of compounds called secondary ethoxylated fatty alcohols, and alkylphenol ethoxylates.

The haircolor dye or "tint" phase allows for exceptionally high levels of water to be used in the vehicle currently in the industry. In this invention the water can range from 75% to about 93 wt %. A preferred level is not less than 80 wt %, but if desired 80-90wt % or 85-92wt % may be used. This high water content allows for the creation of very efficient dying systems. This will translate into more economical use of dye intermediates, less exposure to high levels of dyes for consumers, and improvements in gray coverage and color take on hair. The later seems to stem from the lack of organic solvents and large quantities of surfactants. These ingredients normally absorb a portion of the dye intermediates, rendering them unavailable for the coloration process.

The only surfactant required for adequate viscosity development in the tint phase is selected from a class of materials called alkyl polyglycosides or alkyl glucoside, or glucose esters having a viscosity of from 1000 cps to 10,000 cps. A few other types of surfactants can also develop significant viscosities in this system, however they may not have the best rheological profile, or are not as mild as these ethoxylated sugar compounds. In the alkyl polygycosides the hydrophilic group is a sugar and can be made from polysaccharides, disaccharides, trisaccharides, and various other sugars. Although the "poly" implies these materials are polymers, they generally only have one or two sugar groups in the chain. Examples of some structures are shown in the following illustrations or can be designated as such: $R_1O(R_2O)_t$ $(C_6H_{10}O_5)_y$ where $R_1=C_8-C_{24}$, $R_2=C_2-C_4$ alkylene radical, t=1-10, and y=1-15.

The preferred alkyl polyglycosides are decyl glucoside, lauryl glucoside, caprylyl/capryl glucoside, or a mixture of materials simply known as alkyl glucoside which help to achieve optimum results.

To achieve an adequate mixture viscosity and ideal Theological properties, the glycoside surfactant must be used in combination with a water soluble anionic polymer called carbomers, and most notably manufactured by the Noveon Corporation under the Carbopol name. These can also be described as high molecular weight homo and copolymers of acrylic acid cross linked with a polyalkenyl polyether having a viscosity, as measured in water, at 0.5-1.0% w/v of about 3,000-60,000 mPa s. Examples of these include: Carbopol Ultrez 10, Carbopol 940, Carbopol 941, Carbopol ETD 2020, Carbopol ETP 2050, Carbopol Ultrez 21, and Pemulen 1622. Similar materials are produced by other manufacturers and can go by the CTFA designation of carbomer or acrylates/ C10-30 alkyl acrylate crosspolymer, or other related compounds.

Necessary materials to complete an oxidation dye phase would be the dye intermediate package and antioxidants and chelating agents in order to maintain a good shelf-life of the haircolorant. Antioxidants can include moderate reducing agents such as: sodium sulfite, bisulfite salts, thioglycolate salts, erythorbic acid, ascorbic acid, and similar materials. Chelating agents eliminate metal contaminates from solution so they may not react with dye intermediates or decompose the hydrogen peroxide after mixing with the developer. These are usually EDTA or salts thereof, or compounds such as hydroxyethylidene diphosphonic acid.

The dye intermediate package may include any oxidative primary intermediate or coupler previously employed in the industry. Examples of these would include: 1,7-Naphthalenediol, m-Phenylenediamine, 1-Methyl-2,4-Diaminobenzene, Toluene-2,5-Diamine-p-Phenylenediamine, 2-Chloro-p-Phenylenediamine, N-Phenyl-p-Phenylenediamine, Resorcinol, 4-Chlororesorcinol, 1,2,3-Trihydroxybenzene, o-Aminophenol, m-Aminophenol, p-Aminophenol, 1-Naphthol, 1,5-Naphthalenediol, 2,7-Naphthalenediol, 2,4-Diaminophenol, Hydroquinone, p-Methylaminophenol, 1-Hydroxy-3-carbamoylmethylaminobenzene, Hydroxybenzomorpholine, 1-Hydroxy-3-dimethylaminobenzene, 4-Amino-2-Hydroxytoluene, 3,4-Diaminobenzoic Acid, 6-Hydroxyquinoline, 1-Methyl-2,3-Diaminobenznene, 2-Methyl-5-Hydroxyethylaminophenol, 1,2,4-Trihydroxybenzene, 1-Methoxy-2,5-Diaminobenzene, 1-Amino-4-Diethylaminobenzene,1,3-Dimethyl-2,5-diamino-4-methoxybenzene, 1-Amino-4-methylaminobenzene, 1,3-Dimethyl-2-hydroxy-4-(acetylamino)benzene, Phenyl Methyl Pyrazolone, N-Methoxyethyl-p-phenylenediamine HCl, 1-Dimethylamino-4-aminobenzene, 2,4-Diaminophenoxyethanol HCl, 3-Amino-2,4-Dichlorophenol, 2-Methylresorcinol, 1-Ethyl-2-methoxy-3,5-diaminobenzene, 1-Hydroxy-6-aminonaphthalene-3-sulfonic acid, 6-Methoxy-8-aminoquinoline, 2,6-Dihydroxy4-methylpyridine,1-Methyl-2-methoxy-3,5-diaminobenzene, N,N-Bis(2-Hydroxyethyl)-p-Phenylenediamine, 2,3-Naphthalenediol, 1,3-Dihydroxy-5-methylaminobenzene, 2,4,5,6-Tetraaminopyrimidine, 4-Ethoxy-m-Phenylenediamine, 5-Hydroxy-1,4-benzodioxane, 2-Dimethylamino-4,5,6-triaminopyrimidine, 1-Hydroxy-3-amino-4,6-dichlorobenzene, 1,4-Dihydroxy-2-aminobenzene, 1,4-Dihydroxy-2-methyl amino benzene, 1-Hydroxy-2-amino-4-methoxybenzene, 1-Hydroxy-2,4-diamino-6-methylbenzene, 1-Hydroxy-2,5-diamino-4-methylbenzene, 1-Hydroxy-2,6-diaminobenzene, 6-amino-benomorpholine, 1-amino-3-bis(2'-hydroxyethyl)aminobenzene, N-ethyl-N-(2-hydroxyethyl)amino-4-aminobenzene, 4-Amino-m-Cresol, 6-Amino-m-Cresol, Thymol, 1,3-Bis-(2,4-Diaminophenoxy)-propane, Hydroxyethyl-p-Phenylenediamine Sulfate, 3,4-Methylenedioxyphenol, 2-amino-4-Hydroxyethylaminoanisole, 4-4'-Diaminophenylamine, 2,6-Dimethyl-p-Phenylenediamine, 5-Amino-6-Chloro-o-Cresol, 6-Amino-o-Cresol, Hydroxyethyl-3,4-Methylenedioxyaniline HCl, 2,6-Dihydroxy3,4-Dimethylpyridine, 2,6-Dimethoxy-3,5-Pyridinediamine, 3,4-Methylenedioxyaniline, 2,6-Bis(2-Hydroxyethyloxy)-3,5-Pyridinediamine HCl, 4-Hydroxyindole, 5-Amino-2,6-Dimethoxy-3-hydroxypyridine, 4,6-Bis(2-Hydroxyethoxy)-m-phenylenediamine HCl, 2-Aminoethyl-p-aminophenol HCl, 2,4-Diamino-5-methylphenoxyethanol HCl, Dihydroxyindole, 2-Aminoethyl-p-aminophenol HCl, 2,4-Diamino-5-Methyl-Phenetole HCl, 5-Amino-4-Chloro-o-Cresol, Hydroxyethylaminomethyl-p-aminophenol HCl, 2-Methoxymethyl-p-aminophenol HCl, Hydroxypropyl-Bis-(N-hydroxyethyl-p-phenylenediamine) HCl, 6-Hydroxyindole, 2-Amino-3-Hydroxypyridine, 2,3-Diamino-6-Methoxypyridine, 2,6-Diaminopyridine, 2,5,6-Triamino-4-pyrimidinol Sulfate, Dihydroxyindoline, 5-Amino-5-Fluoro-2-Methylphenol Sulfate, m-Dimethylaminophenylurea, 1-Hydroxyethyl-4,5-Diaminopyrazole Sulfate, and other related compounds.

The dye phase requires the pH to be between 6 and 12 in order to adequately sustain enough alkalinity to swell the hair shaft and decompose the oxidizer so that free oxygen is available for the dye intermediates to couple. More typically the range of pH is 8 to 11. The dye phase may be adjusted to achieve this pH range using a variety of cosmetically acceptable alkalizers that are either organic or inorganic in nature. These can include ethanolamine, triethanolamine, aminomethyl propanol, ammonium hydroxide, carbonates, bicarbonates, and other similar materials.

The developer component of this invention takes advantage of the normal oxidizing agents used in today's permanent haircoloring products. The vast majority of these use hydrogen peroxide for its ease of handling, low cost, and the ability to stabilize the formulas containing this oxidizer. Other oxidizers can replace hydrogen peroxide, such as urea peroxide, persulfates, and even certain enzymes, although formulation efficiencies and efficacies are compromised. For simplicity sake, all examples in this document will use hydrogen peroxide in the 1-12 wt % level based on a peroxide having a strength of 100%, although more typically commercially available hydrogen peroxide will have a strength of 50%, thus formulation concentrations will be 2-24 wt %. If the peroxide obtained does not contain sufficient stabilizers to assist in formulation shelf life, then additional materials for this purpose can be added. These may include EDTA and its salts, sodium stannate, phosphoric acid, etidronic acid, sodium pyrophosphate, and related materials. Usually small quantities of stabilizers, i.e. less than 0.5 wt % are required. The active thickeners that work in conjunction with the dye phase are included in the specific chemical classes called secondary ethoxylated fatty alcohols and alkylphenol ethoxylates. The secondary ethoxylated fatty alcohols are "T" shaped molecules with the following general structure, $C_{12-14}H_{25-29}0(CH_2CH_2O)_xH$ where x is usually 3 to 12. The degree of ethoxylation can vary to a greater extent as long as the resulting HLB of the developer system is within the desired range. The HLB or hydrophilic/lithophilic balance is an industry accepted method for determining a compound's relative degree of water solubility or oil solubility. A numerical value is assigned depending upon this attribute. The lower numbers indicate more oil solubility, and as the numbers get higher the materials get more water soluble. For this class of compounds it was determined experimentally that the preferred HLB range for achieving an optimum mixture viscosity of the combined dye phase and developer phase would preferably be 10.0 to 11.2. The other useful set of compounds are the alkylphenol ethoxylates. The structure is illustrated below.

"R" is either octyl or nonyl, and x is usually 4-9, but again may vary more widely as long as the resulting HLB of the developer is within the prescribed range. For alkyl phenol ethoxylates this range is 9.0-11.2. The level of either type of surfactant used should be in the range of 15-25% of the total formula weight. More preferably the range should be 18-22%. Lastly, the pH of the developer phase needs to be in an area which promotes long term stability of the hydrogen peroxide. This is best in the 2.5-3.5 range, but can vary another ½ of unit on either side. If the pH requires adjustment, this can be accomplished by the use of phosphoric acid or etidronic acid. Usually less than 0.1% is required for an acidic adjustment. If alkali buffering is required, the addition of an ETDA salt or sodium stannate will suffice.

Experimental Procedures and Results:

The following is list of some examples of the dye phase that fall into the previously described criteria for this invention. Example 1 was used throughout the experimental procedures in order to maintain consistent controls.

| Ingredients | Dye Phase Formulas | | | | |
| --- | --- | --- | --- | --- | --- |
| | Medium Brown Ex. 1 Wt % | Light Blonde Ex. 2 Wt % | Black Ex. 3 Wt % | Ash Brown Ex. 4 Wt % | Dark Blonde Ex. 5 Wt % |
| D.I. Water | 83.421 | 84.578 | 80.150 | 86.562 | 84.290 |
| Erythorbic Acid | 0.400 | 0.300 | 0.450 | 0.300 | 0.300 |
| Trisodium EDTA | 0.200 | 0.100 | 0.200 | 0.150 | 0.100 |
| Sodium Sulfite | 0.500 | 0.400 | 0.500 | 0.350 | 0.300 |
| Decyl Glucoside | 9.000 | — | — | 5.000 | — |

-continued

Dye Phase Formulas

| Ingredients | Medium Brown Ex. 1 Wt % | Light Blonde Ex. 2 Wt % | Black Ex. 3 Wt % | Ash Brown Ex. 4 Wt % | Dark Blonde Ex. 5 Wt % |
|---|---|---|---|---|---|
| Lauryl Glucoside | — | 6.000 | — | — | 8.000 |
| Capryly/capryl Glucoside | — | — | 10.000 | — | — |
| Ultrez 10 (Carbomer) | 1.000 | — | — | — | 0.700 |
| Carbomer 940 | — | 0.950 | — | — | — |
| Carbomer ETD 2020 | — | — | 1.050 | 1.000 | — |
| Monoethanolamine | 3.000 | — | — | — | 5.000 |
| Potassium Carbonate | — | — | 1.000 | — | — |
| Ammonium Hydroxide (28% soln.) | — | 7.000 | — | 5.000 | — |
| p-Phenylenediamine | 0.578 | 0.150 | 2.850 | 0.411 | 0.300 |
| m-Aminophenol | 0.289 | 0.030 | 1.200 | 0.129 | 0.060 |
| p-Aminophenol | 0.239 | 0.040 | — | 0.053 | 0.090 |
| N,N-Bis (2-Hydroxyethyl) PPD | 0.190 | 0.025 | — | 0.120 | 0.020 |
| Resorcinol | 0.766 | 0.122 | 1.450 | 0.400 | 0.320 |
| 2-Amino-4-Hydroxy-ethylaminoanisole $SO_4$ | 0.017 | — | 0.700 | 0.025 | — |
| 2-Methylresorcinol | — | 0.005 | — | — | 0.020 |
| 6-Hydroxyindole | — | — | 0.050 | — | — |
| Fragrance | 0.400 | 0.300 | 0.400 | 0.500 | 0.500 |

The following is a list of some examples of the developer phase that are included in this invention. Example 6 was used throughout the experimental procedures in order to maintain consistent controls.

Developer Formulas

| Ingredients | Ex. 6 Wt % | Ex. 7 Wt % | Ex. 8 Wt % | Ex. 9 Wt % | Ex. 10 Wt % |
|---|---|---|---|---|---|
| D.I. Water | 65.760 | 82.900 | 60.000 | 67.760 | 65.760 |
| 50% Hydrogen Peroxide | 14.000 | 2.000 | 24.000 | 12.000 | 10.000 |
| Etidronic Acid | 0.140 | 0.050 | — | 0.140 | 0.140 |
| Disodium EDTA | 0.100 | 0.050 | — | 0.100 | 0.100 |
| $C_{11-15}$ Pareth-3 | 12.000 | — | 4.000 | 9.000 | — |
| $C_{11-15}$ Pareth-9 | 8.000 | — | — | 11.000 | — |
| $C_{11-15}$ Pareth-5 | — | — | 12.000 | — | — |
| Nonoxynol-4 | — | — | — | — | 16.800 |
| Nonoxynol-6 | — | — | — | — | 7.200 |
| Octoxynol-3 | — | 7.500 | — | — | — |
| Nonoxynol-9 | — | 7.500 | — | — | — |
| HLB of formula | 10.3 | 10.35 | 10.025 | 11.05 | 9.5 |

Throughout all of the testing of experiments for this invention, it was determined that two consistency parameters needed to be met in order to deem a particular formula acceptable for commercial use. The first is viscosity as measured by a Brookfield DV-E instrument and spindle T-C at 6 rpm. Salon testing on men and women clients shows a correlation between a specific viscosity range and an appropriate consistency for product application and stay-put properties on the hair. This range is preferably about 7,000 cps-15,000 cps for the combined dye and developer phases as determined by the above noted method in a Brookfield DV-E viscosimeter. In addition, the consistency most preferably exhibits thixotropic Theological properties. This allows for product thinning when force is applied (during the application process) and very high viscosities at rest (good stay-put properties on the hair). The rheology can be tested in the lab, but experience tells us it is far more reliable to examine this parameter on clients in a salon testing atmosphere. Therefore, all mixture viscosities tested include observations on the particular formula under actual use conditions.

The first experiment tests the dye phase and developer's mixture viscosity, the need for the specific developer, and the need for the surfactant/polymer blend in the dye phase. The following chart illustrates the dye formulas used in the experiment.

Dye Phase

| Ingredients | Ex. 1 Wt % | Control Ex. 11 Wt % | Control Ex. 12 Wt % |
|---|---|---|---|
| D.I. Water | 83.421 | 84.421 | 92.421 |
| Erythorbic Acid | 0.400 | 0.400 | 0.400 |
| Trisodium EDTA | 0.200 | 0.200 | 0.200 |
| Sodium Sulfite | 0.500 | 0.500 | 0.500 |
| Decyl Glucoside | 9.000 | 9.000 | — |
| Ultrez 10 (Carbomer) | 1.000 | — | 1.000 |
| Monoethanolamine | 3.000 | 3.000 | 3.000 |
| "p"-Phenylenediamine | 0.578 | 0.578 | 0.578 |
| m-Aminophenol | 0.289 | 0.289 | 0.289 |
| p-Aminophenol | 0.239 | 0.239 | 0.239 |
| N,N-Bis(2-Hydroxyethyl) PPD | 0.190 | 0.190 | 0.190 |
| Resorcinol | 0.766 | 0.766 | 0.766 |
| 2-Amino-4-Hydroyethylaminoanisole $SO_4$ | 0.017 | 0.017 | 0.017 |
| Fragrance | 0.400 | 0.400 | 0.400 |

The next set of examples contains developer formulas, both with and without the thickener system.

Developer Phase

| Ingredients | Example 6 Wt % | Control Ex. 13 Wt % |
|---|---|---|
| D.I. Water | 65.760 | 86.00 |
| 50% Hydrogen Peroxide | 14.000 | 14.000 |
| Etidronic Acid | 0.140 | — |
| Disodium EDTA | 0.100 | — |
| $C_{11-15}$ Pareth-3 | 12.000 | — |
| $C_{11-15}$ Pareth-9 | 8.000 | — |

The results in the following table indicate that both the surfactant and polymer are required to achieve a satisfactory consistency in conjunction with the thickener blend in the developer.

| Dye Phase | Mixture Visc. With Ex. 6 Developer | Salon observations | Mixture Visc. With Ex. 13 Developer | Salon observations |
|---|---|---|---|---|
| Example 1 | 10,330 cps | Good stay-put properties, and easy application | 1780 cps | Too thin & runny |
| Cont. Ex. 11 | 1156 cps | Too thin & runny | 369 cps | Too thin & runny |
| Cont. Ex. 12 | 2410 cps | Too thin & runny | 740 cps | Too thin & runny |

The next experiment tests other surfactants in the dye phase, including other polyglucosides

| Ingredients | Dye Phase Formulas | | | | | | |
|---|---|---|---|---|---|---|---|
| | Control Ex. 14 Wt % | Control Ex. 15 Wt % | Control Ex. 16 Wt % | Control Ex. 17 Wt % | Control Ex. 18 Wt % | Ex. 19 Wt % | Ex. 20 Wt % |
| D.I. Water | 83.421 | 83.421 | 83.421 | 83.421 | 83.421 | 83.421 | 83.421 |
| Erythorbic Acid | 0.400 | 0.400 | 0.400 | 0.400 | 0.400 | 0.400 | 0.400 |
| Trisodium EDTA | 0.200 | 0.200 | 0.200 | 0.200 | 0.200 | 0.200 | 0.200 |
| Sodium Sulfite | 0.500 | 0.500 | 0.500 | 0.500 | 0.500 | 0.500 | 0.500 |
| Quaternium-79 Hydrolyzed Keratin | 9.000 | — | — | — | — | — | — |
| Oleamide MEA[1] | — | 9.000 | — | — | — | — | — |
| Erucamidopropyl[2] Hydroxysultaine | — | — | 9.000 | — | — | — | — |
| Milkamidopropyl[3] betaine | — | — | — | 9.000 | — | — | — |
| PEG-7 Glyceryl[4] Cocoate | — | — | — | — | 9.000 | — | — |
| Lauryl Glucoside | — | — | — | — | — | 9.000 | — |
| Coco Glucoside[5] | — | — | — | — | — | — | 9.000 |
| Ultez 10 (Carbomer) | 1.000 | 1.000 | 1.000 | 1.000 | 1.000 | 1.000 | 1.000 |
| Monoethanolamine | 3.000 | 3.000 | 3.000 | 3.000 | 3.000 | 3.000 | 3.000 |
| p-Phenylenediamine | 0.578 | 0.578 | 0.578 | 0.578 | 0.578 | 0.578 | 0.578 |
| m-Aminophenol | 0.289 | 0.289 | 0.289 | 0.289 | 0.289 | 0.289 | 0.289 |
| p-Aminophenol | 0.239 | 0.239 | 0.239 | 0.239 | 0.239 | 0.239 | 0.239 |
| N,N-Bis (2-Hydroxyethyl) PPD | 0.190 | 0.190 | 0.190 | 0.190 | 0.190 | 0.190 | 0.190 |
| Resorcinol | 0.766 | 0.766 | 0.766 | 0.766 | 0.766 | 0.766 | 0.766 |
| 2-Amino-4-Hydroxyethylaminoanisole $SO_4$ | 0.017 | 0.017 | 0.017 | 0.017 | 0.017 | 0.017 | 0.017 |
| Fragrance | 0.400 | 0.400 | 0.400 | 0.400 | 0.400 | 0.400 | 0.400 |

[1]$CH_3(CH_2)_7CH\!=\!CH(CH_2)_7CONHCH_2CH_2OH$
[2]$CH_3(CH_2)_7CH\!=\!(CH_2)_{11}CONH(CH_2)_3N^+(CH_3)_2CH(OH)CH_2SO_3^-$
[3]$RCONH(CH_2)_3N^+(CH_3)CH_2COO^-$, where R is milk lipids
[4]$RCOOCH_2CHOHCH_2(OCH_2CH_2)_7OH$ where R represents the coconut radical
[5]an alkyl glycoside where the alkyl group is derived from coconut fatty alcohols The results from the evaluation of examples 14 through 20 indicate that some viscosity is generated by commonly used surfactants from the haircare industry, however the best results are obtained from materials in the polyglucoside family. These would include the lauryl glucoside and coco glucoside in examples 19 and 20. Even with these materials the thickener package included in Example 6 is required to achieve good consistency results. With the typical developer of example 13, the viscosities drop off considerably.

| Dye Phase | Mixture Visc. With Ex. 6 Developer | Salon observations | Mixture Visc. With Ex. 13 Developer | Salon observations |
|---|---|---|---|---|
| Example 14 | 4500 cps | Slightly thin and runny | 344 cps | Too thin & runny |
| Example 15 | 3560 cps | Slightly thin and runny | 2300 cps | Too thin & runny |
| Example 16 | 6500 cps | Slightly thin and runny | 1488 cps | Too thin & runny |
| Example 17 | 5600 cps | Slightly thin and runny | 1369 cps | Too thin & runny |
| Example 18 | 4700 cps | Slightly thin and runny | 919 cps | Too thin & runny |
| Example 19 | 11,400 cps | Good stay put properties, and easy application | 2100 cps | Too thin & runny |
| Example 20 | 12,320 cps | Good stay put properties, and easy application | 2240 cps | Too thin & runny |

Experimental data has shown that surfactants from the alkyl polyglycoside group produce the best results in achieving an appropriate mixture consistency for a haircoloring product when used within the specified dye/developer system. The following experiment identifies the most effective polymers to be used in conjunction with a surfactant in the dye phase. The following table lists the formulas that were examined.

| Ingredients | Ex. 21 Wt % | Ex. 22 Wt % | Ex. 23 Wt % | Ex. 24 Wt % | C. Ex. 25 Wt % | C. Ex. 26 Wt % | C. Ex. 27 Wt % | C. Ex. 28 Wt % | C. Ex. 29 Wt % |
|---|---|---|---|---|---|---|---|---|---|
| D.I. Water | 83.421 | 83.421 | 83.421 | 83.421 | 81.421 | 83.421 | 81.421 | 74.421 | 81.421 |
| Erythorbic Acid | 0.400 | 0.400 | 0.400 | 0.400 | 0.400 | 0.400 | 0.400 | 0.400 | 4.000 |
| Trisodium EDTA | 0.200 | 0.200 | 0.200 | 0.200 | 0.200 | 0.200 | 0.200 | 0.200 | 0.200 |
| Sodium Sulfite | 0.500 | 0.500 | 0.500 | 0.500 | 0.500 | 0.500 | 0.500 | 0.500 | 0.500 |
| Decyl Glucoside | 9.000 | 0.500 | 0.500 | 0.500 | 0.500 | 0.500 | 0.500 | 0.500 | 0.500 |
| Carbomer 940 | 1.000 | — | — | — | — | — | — | — | — |
| Carbomer EDT2020 | — | 1.000 | — | — | — | — | — | — | — |
| Carbopol Pemulen 1622 | — | — | 1.000 | — | — | — | — | — | — |
| Ultrez 21 Carbomer | — | — | — | 1.000 | — | — | — | — | — |
| Aculyn 28[1] | — | — | — | — | 3.000 | — | — | — | — |
| Hydroxyethyl Cellulose | — | — | — | — | — | 1.000 | — | — | — |
| Aculyn 22[2] | — | — | — | — | — | — | 3.000 | — | — |
| Aculyn 46[3] | — | — | — | — | — | — | — | 10.000 | — |
| Structure 3001[4] (National Starch) | — | — | — | — | — | — | — | — | 3.000 |
| Monoethanolamine | 3.000 | 3.000 | 3.000 | 3.000 | 3.000 | 3.000 | 3.000 | 3.000 | 3.000 |
| p-Phenylenediamine | .578 | 0.578 | 0.578 | 0.578 | 0.578 | 0.578 | 0.578 | 0.578 | 4.578 |
| m-Aminophenol | 0.289 | 0.289 | 0.289 | 0.289 | 0.289 | 0.289 | 0.289 | 0.289 | 0.289 |
| p-Aminophenol | 0.239 | 0.239 | 0.239 | 0.239 | 0.239 | 0.239 | 0.239 | 0.239 | 0.239 |
| N,N-Bis (2 hydroxyethyl) PPD | 0.190 | 0.190 | 0.190 | 0.190 | 0.190 | 0.190 | 0.190 | 0.190 | 0.190 |
| Resorcinol | 0.766 | 0.766 | 0.766 | 0.766 | 0.766 | 0.766 | 0.766 | 0.766 | 0.766 |
| 2-Amino-4-Hydroxyethylaminoanisole $SO_4$ | 0.017 | 0.017 | 0.017 | 0.017 | 0.017 | 0.017 | 0.017 | 0.017 | 0.017 |
| Fragrance | 0.400 | 0.400 | 0.400 | 0.400 | 0.400 | 0.400 | 0.400 | 0.400 | 0.400 |

C. Ex = Control Example
[1] acrylates/ceteth-20 $(CH_3(CH_2)_{14}CH_2(OCH_2CH)_{20}OH$ methacrylates copolymer
[2] acrylates steareth-20 $(CH_3(CH_2)_{16}CH_2(OCH_2CH)_{20}OH$ methacrylates copolymer
[3] PEG-150/stearyl/SSMDI copolymer $H(OCH_2CH_2)_{150}/CH2OH(CH_3(CH_2)_{16}CH_2OH/OCNC_6H_4CH_2C_6H_4NCO)$
[4] acrylates/ceteth-20 itaconate Results from consistency testing of examples 21 through 29 are illustrated in the next chart. All of the water soluble anionic polymers (carbomers & Pemulen) did produce the most acceptable mixture viscosity and salon results when used in conjunction with the invention's developer prototype as shown in Example 6. As with other dye phases that are contained within this system, the viscosity diminishes significantly when alternate developers are used, such as Example 13. We can also determine that other water soluble polymers with no charge, such as the cellulose compound used in Example 26, do not develop the necessary rheological properties required for haircoloring products. This is also true for dispersed anionic polymers that are included in examples 25, 27, 28, and 29.

| Dye Phase | Mixture Visc. With Ex. 6 Developer | Salon observations | Mixture Visc. With Ex. 13 Developer | Salon observations |
|---|---|---|---|---|
| Example 21 | 9450 cps | Good stay-put properties, and easy application | 2390 cps | Too thin & runny |
| Example 22 | 9500 cps | Good stay-put properties, and easy application | 1940 cps | Too thin & runny |
| Example 23 | 11,700 cps | Good stay-put properties, and easy application | 2390 cps | Too thin & runny |
| Example 24 | 7800 cps | Good stay-put properties, and easy application | 1140 cps | Too thin & runny |
| C. Ex. 25 | 4140 cps | Slightly thin and runny | 770 cps | Too thin & runny |
| C. Ex. 26 | 4050 cps | Good stay put properties, and easy application | 840 cps | Too thin & runny |
| C. Ex. 27 | 4820 cps | Slightly thin and runny | 1160 cps | Too thin & runny |
| C. Ex. 28 | 3250 cps | Slightly thin and runny | 800 cps | Too thin & runny |
| C. Ex. 29 | 3280 cps | Too thin and runny | 800 cps | Too thin & runny |

Figure 1:
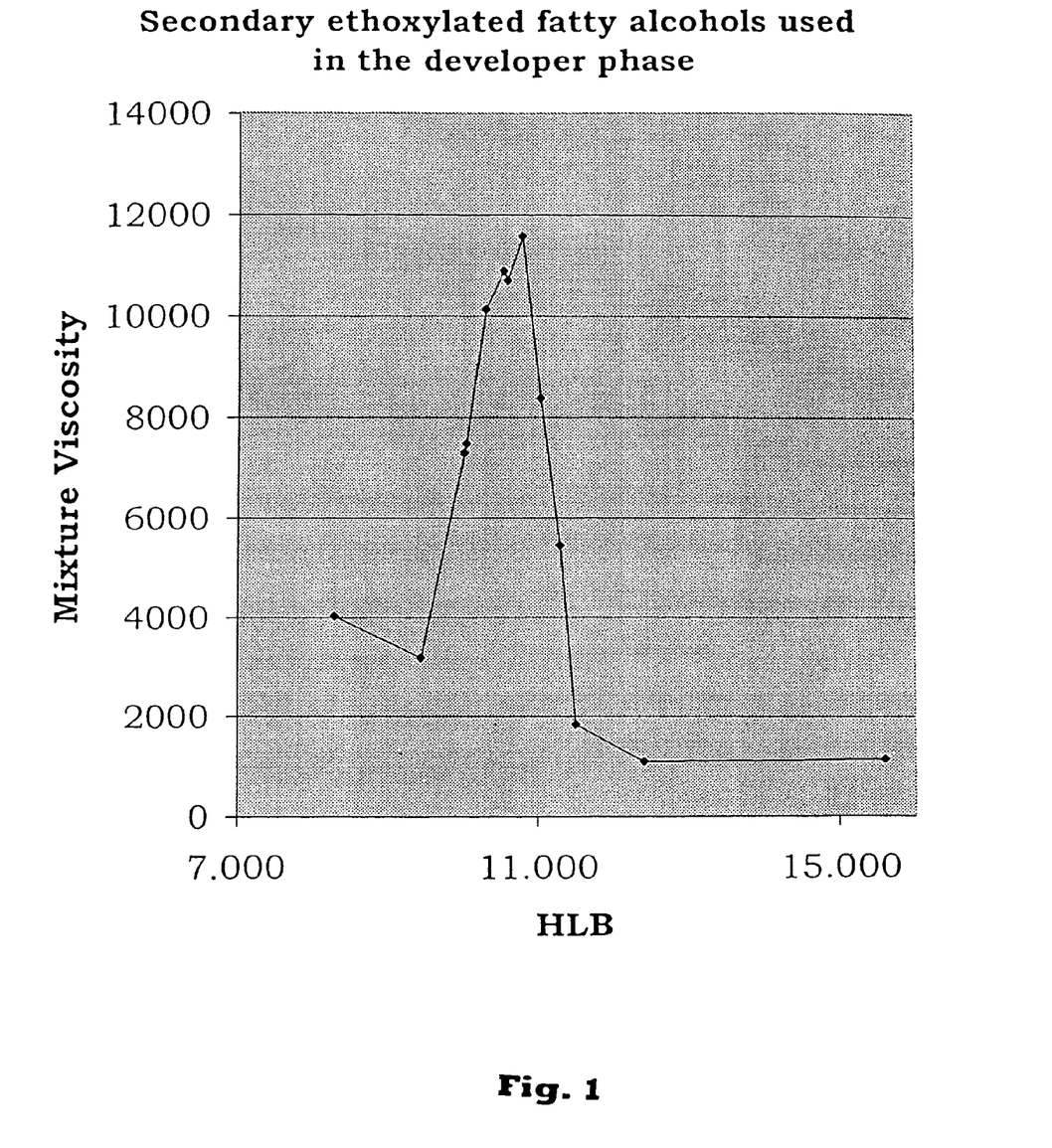
FIG. 1 is a graph of the mixture viscosity vs. the HLB of the secondary fatty alcohols used in the developer phase.
Figure 2:
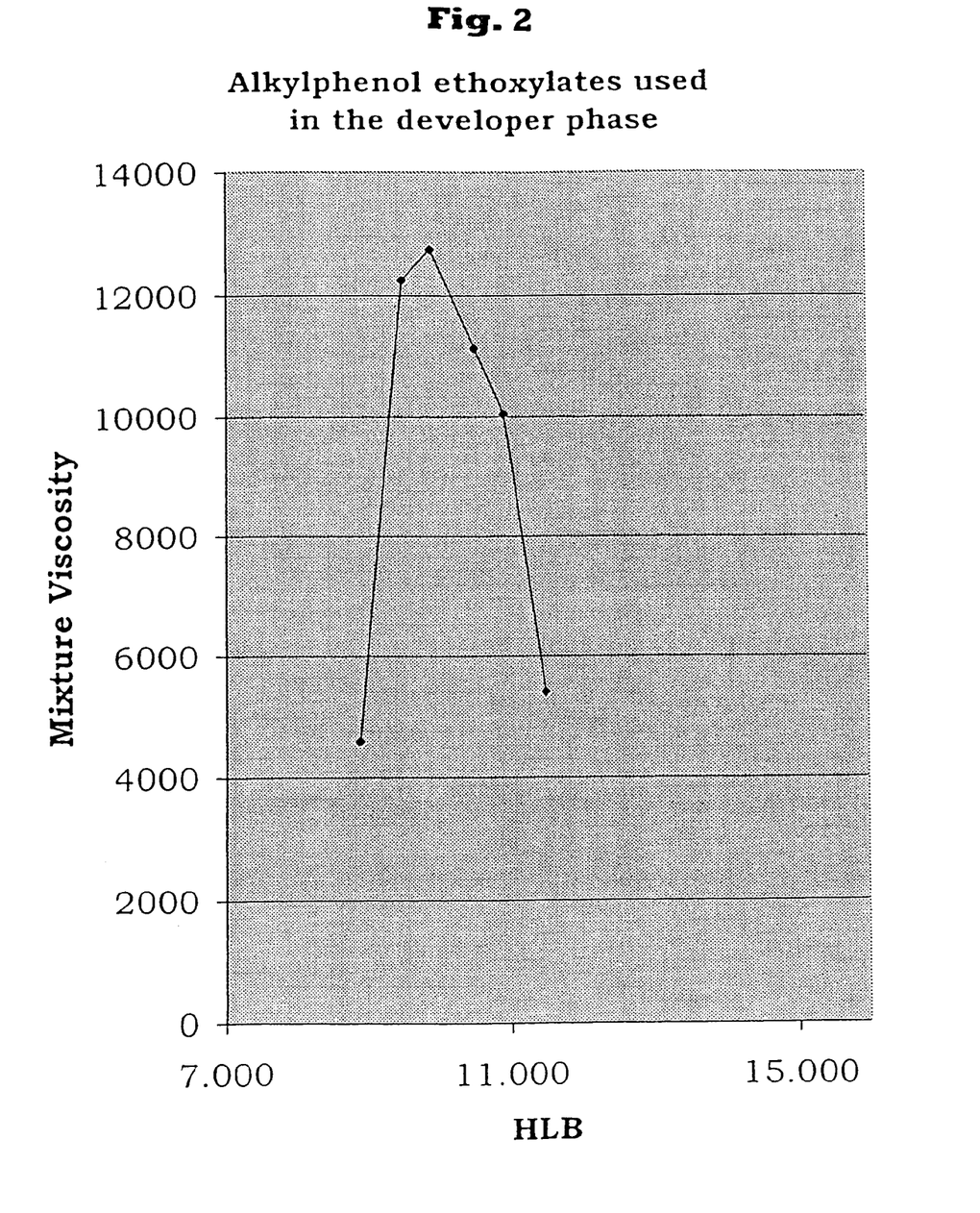
FIG. 2 is a graph of the mixture viscosity vs. the HLB of the alkylphenol ethoxylates in the developer phase

The preceding data adequately identifies the scope of this invention for the dye phase of this system. Since a specific developer is required for this type of product, the next set of experiments and data accompanying this information will concentrate on the oxidizer vehicle. This material will deal only with the secondary ethoxylated fatty alcohols and alkylphenol ethoxylates. Besides the rheological properties that are generated upon mixing the developer phase with the dye phase, the selection of materials used in the developer depend heavily upon compatibility with the oxidizer. This will automatically rule out virtually all polymers with the exception of the water insoluble acrylate copolymers referred to in earlier inventions. Other materials that were screened and found to be stable with hydrogen peroxide include: fatty esters ($C_{8-32}$), linear fatty alcohols (both saturated and unsaturated, $C_{8-32}$), linear ethoxylated fatty alcohols, and natural and synthetic waxes. At low concentrations in the developer phase, all of these materials developed very low viscosities when mixed with the invention's dye phase. At high enough concentrations to generate mixture viscosities with adequate stay-put properties, the consistencies were all too creamy and non-shear thinning to allow for easy application with a typical developer bottle and tip. The two types of surfactants that were determined to be useful in this invention both have similar physical characteristics, as they seem to work best on the edge of water solubility. If the developer surfactant system is too water soluble or too oil soluble, its effectiveness in thickening the dye phase is extremely diminished. This is very visually apparent when the mixture viscosity of the dye phase (example 1) plus developer is plotted vs. the HLB of the developer's surfactant combination. The following tables, charts, and FIGS. 1 and 2 illustrate the narrow range at which these formulations are particularly useful.

-continued

| Viscosity vs HLB varying secondary fatty alcohol ethoxylation | | |
|---|---|---|
| Formula | HLB | Mixture Viscosity with example 1 |
| Example 36 | 10.8 | 11,580 cps |
| Example 37 | 11.05 | 8380 cps |
| Example 38 | 11.30 | 5440 cps |
| Example 39 | 11.5 | 1840 cps |
| Example 40 | 12.4 | 1090 cps |
| Example 41 | 13.3 | 1130 cps |
| Example 42 | 14.7 | 1310 cps |
| Example 43 | 15.6 | 1140 cps |

| High Aqueous Developer Formulas using Secondary ethoxylated fatty alcohols | | | | | | | | |
|---|---|---|---|---|---|---|---|---|
| Ingredients | C. Ex. 30 Wt % | C. Ex. 31 Wt % | Ex. 32 Wt % | Ex. 33 Wt % | Ex. 6 Wt % | Ex. 34 Wt % | Ex. 35 Wt % | Ex. 36 Wt % |
| D.I. Water | 65.760 | 65.760 | 65.760 | 65.760 | 65.760 | 65.760 | 65.760 | 65.760 |
| 50% Hydrogen Peroxide | 14.000 | 14.000 | 14.000 | 14.000 | 14.000 | 14.000 | 14.000 | 14.000 |
| Erythorbic Acid | 0.140 | 0.140 | 0.140 | 0.140 | 0.140 | 0.140 | 0.140 | 0.140 |
| Disodium EDTA | 0.100 | 0.100 | 0.100 | 0.100 | 0.100 | 0.100 | 0.100 | 0.100 |
| $C_{11-15}$ Pareth-3 | 20.000 | 10.000 | 5.000 | 13.000 | 12.000 | 11.000 | — | 10.000 |
| $C_{11-15}$ Pareth-5 | — | 10.000 | 15.000 | — | — | — | 20.000 | — |
| $C_{11-15}$ Pareth-9 | — | — | — | 7.000 | 8.000 | 9.000 | — | 10.000 |

| Ingredients | Control Ex. 37 | Control Ex. 38 | Control Ex. 39 | Control Ex. 40 | Control Ex. 41 | Control Ex. 42 | Control Ex. 43 |
|---|---|---|---|---|---|---|---|
| D.I. Water | 65.760 | 65.760 | 65.760 | 65.760 | 65.760 | 65.760 | 65.760 |
| 50% Hydrogen Peroxide | 14.000 | 14.000 | 14.000 | 14.000 | 14.000 | 14.000 | 14.000 |
| Erythorbic Acid | 0.140 | 0.140 | 0.140 | 0.140 | 0.140 | 0.140 | 0.140 |
| Disodium EDTA | 0.100 | 0.100 | 0.100 | 0.100 | 0.100 | 0.100 | 0.100 |
| $C_{11-15}$ Pareth-3[1] | 9.000 | 8.000 | — | — | — | — | — |
| $C_{11-15}$ Pareth-5[2] | — | — | 10.000 | — | — | — | — |
| $C_{11-15}$ Pareth-7[3] | — | — | 10.000 | 20.000 | — | — | — |
| $C_{11-15}$ Pareth-9[4] | 11.000 | 12.000 | — | — | 20.000 | — | — |
| $C_{11-15}$ Pareth-12[5] | — | — | — | — | — | 20.000 | — |
| $C_{11-15}$ Pareth-15[6] | — | — | — | — | — | — | 20.000 |

[1] $C_{11-15}H_{24-30}O(CH_2CH_2O)_3H$
[2] $C_{11-15}H_{24-30}O(CH_2CH_2O)_5H$
[3] $C_{11-15}H_{24-30}O(CH_2CH_2O)_9H$
[4] $C_{11-15}H_{24-30}O(CH_2CH_2O)_7H$
[5] $C_{11-15}H_{24-30}O(CH_2CH_2O)_{12}H$
[6] $C_{11-15}H_{24-30}O(CH_2CH_2O)_{15}H$

| Viscosity vs HLB varying secondary fatty alcohol ethoxylation | | |
|---|---|---|
| Formula | HLB | Mixture Viscosity with example 1 |
| Example 30 | 8.3 | 4020 cps |
| Example 31 | 9.45 | 3190 cps |
| Example 32 | 10.025 | 7300 cps |
| Example 33 | 10.050 | 7480 cps |
| Example 6 | 10.3 | 10,130 cps |
| Example 34 | 10.55 | 10,890 cps |
| Example 35 | 10.6 | 10,700 cps |

| High Aqueous Developer Formulas using Alkylphenol Ethoxylates | | | | | | |
|---|---|---|---|---|---|---|
| Ingredients | Control Ex. 44 Wt % | Ex. 45 Wt % | Ex. 46 Wt % | Ex. 47 Wt % | Ex. 48 Wt % | Control Ex. 49 Wt % |
| D.I. Water | 65.760 | 65.760 | 65.760 | 65.760 | 65.760 | 65.760 |
| 50% Hydrogen Peroxide | 14.000 | 14.000 | 14.000 | 14.000 | 14.000 | 14.000 |
| Erythorbic Acid | 0.140 | 0.140 | 0.140 | 0.140 | 0.140 | 0.140 |
| Disodium EDTA | 0.100 | 0.100 | 0.100 | 0.100 | 0.100 | 0.200 |
| Nonoxynol-4 | 20.000 | 14.000 | 10.000 | 12.000 | 10.000 | — |
| Nonoxynol-6 | — | 6.000 | 10.000 | — | — | 14.000 |
| Nonoxynol-9 | — | — | — | 8.00 | 10.000 | 6.000 |

Viscosity vs HLB varying alkylphenol ethoxylation

| Formula | HLB | Mixture Viscosity with example 1 |
|---|---|---|
| Example 44 | 8.9 | 4590 cps |
| Example 45 | 9.5 | 12,250 cps |
| Example 46 | 9.9 | 12,750 cps |
| Example 47 | 10.5 | 11,130 cps |
| Example 48 | 10.9 | 10,050 cps |
| Example 49 | 11.5 | 5410 cps |

All of the necessary parameters for this invention have been experimentally identified. One unexpected advantage of the haircolor/developer system is the dye efficiency, and improved gray coverage resulting from this efficiency. In order to demonstrate this phenomenon that was first observed during salon testing of the various formula examples, the standard medium brown dye package used in example 1 was compared to a more traditional haircolor vehicle (approx. 25% water) as shown in example 50, and another high aqueous dye (example 51) that uses a non-water soluble anionic polymer in the developer phase. The formulas are compared below.

| Ingredients | Example 1 Wt % | Control Ex. 50 Wt % | Control Ex. 51 Wt % |
|---|---|---|---|
| D.I. Water | 83.421 | 25.421 | 60.421 |
| Ethanolamine | 3.000 | 8.000 | 2.000 |
| Trisodium EDTA | 0.200 | 0.200 | 0.200 |
| Erythorbic Acid | 0.400 | 0.400 | 0.400 |
| Sodium Sulfite | 0.500 | 0.500 | 0.500 |
| Decyl Glucoside | 9.000 | — | — |
| Ultrez 10 (Carbomer) | 1.000 | — | — |
| Sodium Laureth Sulfate | — | — | 9.000 |
| Sodium Lauryl Sulfate | — | — | 19.000 |
| Lauramide DEA | — | — | 6.000 |
| Oleic Acid | — | 17.000 | — |
| Oleic Alcohol | — | 2.000 | — |
| Oleth-3 | — | 17.000 | — |
| Cocobetaine | — | 1.000 | — |
| Polyquaternium-22 | — | 1.000 | — |
| Ethoxydiglycol | — | 25.000 | — |
| Fragrance | 0.400 | 0.400 | 0.400 |
| "p"-Phenylenediamine | 0.578 | 0.578 | 0.578 |
| m-Aminophenol | 0.289 | 0.289 | 0.289 |
| p-Aminophenol | 0.239 | 0.239 | 0.239 |
| N,N-Bis(2-Hydroxyethyl) PPD | 0.190 | 0.190 | 0.190 |
| Resorcinol | 0.766 | 0.766 | 0.766 |
| 2-Amino-4-Hydroyethyl-aminoanisole SO$_4$ | 0.017 | 0.017 | 0.017 |

Experimental Procedure:

Swatches (3 grams) were prepared from human 90% gray hair. The three formulas were mixed 1:1 with their appropriate developer and immediately applied to the hair swatches for 10 minutes. The swatches were then rinsed, shampooed, and dried with a hair dryer. The color was measured on an untreated swatch and the three formulas using a Minolta Spectrophotometer, model #CM-508d. As is the industry standard, the Hunter L,a,b scale was used where "L" is the lightness (+lighter,–darker), "a" indicates relative amounts of red (+) or green (–), and "b" indicates relative amounts of yellow (+) or blue(–). E (total color value) can be calculated as $E=(L^2+a^2+b^2)^{1/2}$, a consequent delta E is the total color change or difference from the untreated hair and the dyed hair. The results are displayed in the following table:

Spectrophotometer readings using the Hunter l, a, b scale

| Sample | L Value | a value | b value | Delta L | Delta E |
|---|---|---|---|---|---|
| Untreated 90% Gray hair | 53.4 | –0.3 | 9.8 | — | — |
| Example | 28.8 | 3.2 | 4.9 | 24.5 | 25.2 |
| Example 50 | 41.3 | 2.3 | 7.8 | 12.1 | 12.5 |
| Example 51 | 33.5 | 2.5 | 4.8 | 19.9 | 20.7 |

Example 1 produces a significantly greater change in color from an untreated swatch than the formula with low water content and even the other high aqueous type. This means that Example 1 is achieving greater color deposit and coverage.

Manufacturing Procedures:

The manufacturing procedures for typical formulas included in this invention are as follows:

Example 1, high aqueous haircolor vehicle:
1) To a jacketed stainless steel batch vessel fitted with a counter rotating creme mixer or propeller mixer, add all of the D.I. water and disperse the anionic polymer. The dispersion is then heated to 55° to 65° C.
2) The antioxidants and chelating agents are then dissolved in the batch. After dissolution is complete, this procedure is repeated for all of the dye intermediates. The batch temperature is maintained until the dyes have completely dissolved.
3) Cool the batch to 55° and add the surfactant. Continue cooling the batch to 40°-43° C. and add the alkalizer and fragrance. Mix until uniform.

Example 6, developer for high aqueous system:
1) To a jacketed stainless steel batch vessel fitted with a counter rotating creme mixer or propeller mixer, passivate the vessel with 10% hydrogen peroxide solution for 24 hours. After the pasivation process, drain and dry the tank. To this vessel add the D.I. Water and dissolve the chelating agent with mixing at room temperature. Upon dissolution add the etidronic acid and mix until uniform.
2) With mixing add the surfactants in the following order, $C_{11-15}$ Pareth-9 and $C_{11-15}$ Pareth-3. If other materials are used, the most water soluble should be added first. Mix until uniform.
3) Add the hydrogen peroxide solution to the batch vessel with mixing. Continue mixing until uniform.

The invention claimed is:

1. An oxidation haircolor system which consists essentially of a flowable dye phase and a flowable developer phase having the following ingredients in weight percent based on the total weight of the composition:
   dye phase:
   a) 5-10% of a water soluble nonionic surfactant
   b) 0.5-1.0% of a water soluble anionic polymer
   c) 75-90% water
   d) 0.001-10% of oxidation dye intermediates
   e) 0.1-1.0% of antioxidants and stabilizers developer phase:
   a) 15-25% of secondary ethoxylated fatty alcohols
   c) 1-12% of an oxidizer
   d) 60-84% water wherein the mixture viscosity of the dye and developer phases when combined is 7,000 cps-15,000 cps.

2. An oxidation haircolor system as defined in claim 1 wherein the water soluble nonionic surfactant is selected from the group consisting of alkyl polyglycosides.

3. An oxidation haircolor system as defined in claim 1 wherein the water soluble anionic polymer is a high molecular weight carbomer.

4. An oxidation haircolor system as defined in claim 1 wherein the oxidation dye intermediate is an oxidation coupler or primary intermediate that produces color when developed on human hair.

5. An oxidation haircolor system as defined in claim 1 wherein the oxidation dye phase contains an alkalizer.

6. An oxidation haircolor system as defined in claim 1 wherein the developer phase contains secondary ethoxylated fatty alcohols having the general structure; $C_{12-14}H_{25-29}O(CH_2CH_2O)_xH$ where x is usually 3 to 12.

7. An oxidation haircolor system as defined in claim 1 wherein the developer phase contains a water soluble oxidizer.

8. An oxidation haircolor system as defined in claim 7 wherein the oxidizer is hydrogen peroxide.

9. An oxidation haircolor system as defined in claim 7 where the composition contains a chelating agent.

10. An oxidation haircolor system as defined in claim 7 wherein the composition contains a peroxide stabilizer selected from the group consisting of sodium stannate, etidronic acid, phosphoric acid and sodium pyrophosphate.

11. An oxidation haircolor system as defined in claim 1 wherein the dye phase and developer phase are both flowable liquids.

12. An oxidation haircolor system as defined in claim 1 wherein the dye phase has a pH of 6.0-12.0, and the developer phase has a pH of 2.0-4.0.

13. An oxidation haircolor system as defined in claim 1 and the developer phase includes a secondary ethoxylated fatty alcohols and the formula has a HLB range of 10.0-11.2.

14. An oxidation haircolor system as defined in claim 1 wherein the developer phase includes alkylphenol ethoxylates and the formula has an HLB range of 9.0-11.2.

15. An oxidation haircolor system as defined in claim 1 where the rheological properties of combined dye and developer phases is sufficiently thixotropic to allow for shear thinning when force is applied during the application process and when at rest has a sufficiently high viscosity that provide good stay-put properties on the hair.

* * * * *